United States Patent [19]

Ikeguchi et al.

[11] 4,220,858
[45] Sep. 2, 1980

[54] APPARATUS FOR DETECTING CHANGE IN WATER QUALITY

[75] Inventors: Takashi Ikeguchi; Shunsuke Nogita; Kouji Otani; Shigeoki Nishimura, all of Hitachi, Japan

[73] Assignee: Hitachi, Ltd., Japan

[21] Appl. No.: 876,104

[22] Filed: Feb. 8, 1978

[30] Foreign Application Priority Data

Feb. 10, 1977 [JP] Japan ................................. 52-13921

[51] Int. Cl.² ...................... G01N 21/26; G01N 33/18
[52] U.S. Cl. ....................................... 250/343; 422/68
[58] Field of Search ............ 23/253 R, 230 R, 232 C, 23/230 PC; 422/68, 83; 250/343; 195/127

[56] References Cited

U.S. PATENT DOCUMENTS

| | | | |
|---|---|---|---|
| 3,322,504 | 5/1967 | Capuano | 23/230 R |
| 3,746,510 | 7/1973 | June | 23/230 R |
| 3,784,359 | 1/1974 | Parth | 23/230 PC X |
| 3,963,927 | 6/1976 | Bruce et al. | 250/343 X |
| 4,063,891 | 12/1977 | Becker et al. | 23/230 R X |

*Primary Examiner*—Joseph Scovronek
*Attorney, Agent, or Firm*—Craig & Antonelli

[57] ABSTRACT

Sample water is introduced into a water bath in which aquatics live, and a gas sparingly soluble in water and giving no effect upon biological activities of aquatics is supplied to the water bath. The supplied gas and carbon dioxide gas generated by the biological activities of aquatics are collected, and a change in water quality of the sample water is detected from a concentration of carbon dioxide thus collected.

Change in water quality of sample water can be rapidly detected thereby, which can be applied to detection of whether toxic materials are contained, for example, in river water flowing into a water purification plant, or not.

11 Claims, 9 Drawing Figures

LAPSE OF TIME AFTER INTRODUCING 1mg CYANIDE (hr)

APPARATUS FOR DETECTING CHANGE IN WATER QUALITY

LIST OF PRIOR ART REFERENCES (37 CFR 1.56 (a))

The following reference is cited to show the state of the art:

U.S. Pat. No. 3,805,224

BACKGROUND OF THE INVENTION

This invention relates to an apparatus for detecting a change in water quality, and particularly to an apparatus for detecting a change in water quality, applicable to detect, at an early stage, a change in water quality due to inflow of toxic materials soluble in water.

Recent upgrading of the standard of living has caused accidental infiltrations of phenol, cyanide or other toxic materials in water purification plants, sewage treatment plants, fish breeding ponds, etc. which have been serious problems. Such problems are inevitable in the social life of human beings, and it has been keenly desired to detect, at an early stage, a change in water quality due to inflow of the toxic materials.

Heretofore, the inflow of toxic materials soluble in water has been detected, for example, by a voluntary notification from a polluting source of toxic materials, report by river monitors, monitoring of growth states of crucian carps, goldfishes, etc. under breeding, detection by water examination in water examination laboratories, etc. However, these detections are all based on off-line measurement methods, and have problems, because they mostly depend upon human labor and require skillfulness and much time in the detection.

As means for solving these problems, a technique of measurement by a photoelectric device and a technique of measurement utilizing ultrasonic waves have been proposed. These two techniques are based on breeding fishes in a water bath, and observing movements of the fishes. That is, the former technique is to detect a change in water quality by irradiating light beams through water and measuring number of interruptions of the light beams by movements of the fishes by means of a photoelectric device. The technique cannot make a measurement in a dark place, and cannot be applied to the fishes living in a hidden place or at a bottom of the bath for most of time. Furthermore, the technique has a disadvantage of failing to make distinction of whether the interruption of light beams is due to a change in water quality or biological activities (for example, eating, sleeping, or movement) of the fishes.

The latter technique utilizing the ultrasonic waves is disclosed in U.S. Pat. No. 3,805,224, entitled "Method and apparatus for monitoring biological activity", where ultrasonic waves are emitted through a water bath, and their reflection or absorption patterns are measured to observe the mobility of fishes and consequently detect a change in water quality. The technique has such disadvantages that the fishes as the target must have a considerably large mobility and a size large enough to reflect or absorb the ultrasonic waves, the apparatus must be also of large scale and complicated structure, and further it takes much time in obtaining the reflection or absorption patterns of the ultrasonic waves and also much skill and many experiences in the operation.

SUMMARY OF THE INVENTION

An object of the present invention is to provide an apparatus for detecting a change in water quality, which can simply detect a change in water quality of sample water due to inflow of soluble toxic materials.

The present invention is characterized by introducing sample water into a water bath in which aquatics live, and detecting a change in water quality by a concentration of carbon dioxide generated by respiratory action of the aquatics in the water bath.

Other objects and characteristics of the present invention will be made obvious from the following detailed description by way of the accompanying drawings.

DETAILED DESCRIPTION OF THE INVENTION

At first, a basic concept of the present invention will be described.

Figure 1:
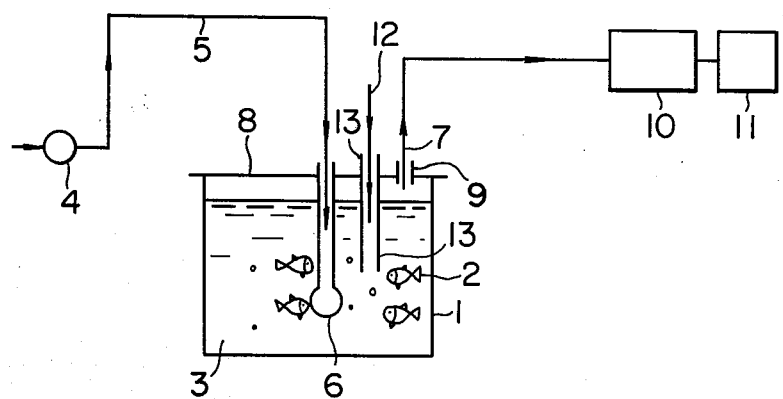
FIG. 1 is a schematic flow diagram of an examination setup for measuring a breathing rate of goldfishes.

In FIG. 1, a schematic flow diagram of an examination setup employed by the present inventors is shown. Four goldfishes 2 (total weight: 12 g) having almost same sizes are bred as aquatics in a tightly sealed water bath 1 having an inside volume of 1 l. Industry grade water chemically equilibrated by aeration for 72 hours is used as water 3. Air 5 is supplied to the water bath 1 at its lower part through an air stone 6, and an air pump 4 is used as an air supplying means. The air 5 supplied into the water bath 1 acts to dissipate carbon dioxide generated by respiratory activities of the goldfishes 2 to the atmosphere from the water.

More concretely, carbon dioxide exists in water as free carbonic acid, and its content depends upon carbon dioxide partial pressure of the atmosphere in contact with the water surface, water temperature, etc. When the goldfishes 2 produce carbon dioxide in the equilibrium state of free carbonic acid in water, there appears a temporary state of supersaturation. If the water is aerated and stirred by the air incapable of undergoing a chemical reaction with carbon dioxide at that time, the free carbonic acid in the amount corresponding to said supersaturation is all dissipated into the atmosphere.

The top of the water bath 1 is tightly sealed by a cover 8, and thus a sample gas 7 comprising the air and carbon dioxide dissipated into the gas phase in the water bath 1 in said manner is withdrawn through an outlet 9 at the cover 8. The sample gas 7 cannot be withdrawn through other than the sample gas outlet 9 as shown in FIG. 1, and is all led to a carbon dioxide meter 10. A non-dispersing type infrared spectrometer is used as the carbon dioxide meter 10, and measures a carbon dioxide concentration of the sample gas 7. The values of the measurement are recorded in a recorder 11. A tube 13 for adding toxic materials is provided at the water bath 1 through the cover 8, and the lower end of the tube 13 reaches the lower part of the water bath 1.

In said experimental setup, 1 mg of cyanide is added to the water once through the tube 13 as toxic materials 12 to measure a transient response of breathing rate of the goldfishes. The results as shown in FIG. 2 are obtained.

Figure 2:
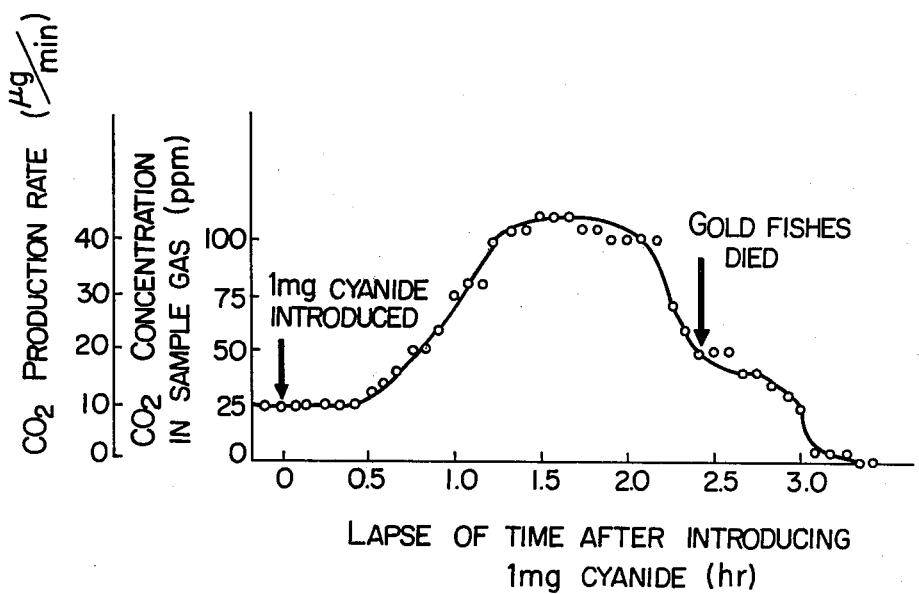
FIG. 2 is a characteristic diagram showing $CO_2$ production rate of goldfishes when a cyanide is introduced to the examination setup of FIG. 1.

In FIG. 2, amount ($\mu$g) of carbon dioxide produced per goldfish per minute and concentration (ppm) of carbon dioxide in the sample gas 7 are shown on the ordinate. The values of the concentration of carbon dioxide shown in FIG. 2 indicate only the concentration of carbon dioxide produced by the respiratory activity of the goldfish by subtracting the concentration of carbon dioxide in the air 5, i.e. 320 ppm, from the values of measurement. Carbon dioxide will be hereinafter referred to as "$CO_2$".

FIG. 2 shows that the respiratory activity of goldfish becomes vigorous 0.5 hours after the addition of the cyanide, and the $CO_2$ concentration starts to increase and reaches a peak 1.3 hours thereafter, and that 2.4 hours thereafter, all the goldfishes 2 have died, and the $CO_2$ concentration becomes zero. This characteristic will be described below in terms of $CO_2$ production rate per goldfish (weight: 3 g). The $CO_2$ production rate is 9 $\mu$g/min before the cyanide introduction, but is a maximum of 41 $\mu$g/min after the cyanide introduction. That is, it is apparent that the maximum $CO_2$ production, after cyanide introduction, is about 4-fold the production rate prior to cyanide introduction. The $CO_2$ production rate is proportionate to the $CO_2$ concentration. That is, the $CO_2$ concentration also becomes about 4-fold. There is a time lag of 0.5 hours between the cyanide introduction and the start of increase in $CO_2$ concentration, and also a time lag of 0.9 hours between the death of goldfishes and the reaching of the zero $CO_2$ concentration, and these are due to the excessive size of the conduit used for leading the sample gas to the $CO_2$ meter 10 and the excessive volume of the gas phase section in the water bath 1.

The experimental results shown in FIG. 2 are based on the introduction of 1 mg of cyanide to the water bath having an inside volume of 1 l. Increments in the $CO_2$ concentration and their rate depend upon the kind and amount of toxic materials. Furthermore, an introduction of highly toxic materials will kill the goldfishes instantaneously, and thus the $CO_2$ concentration will be decreased without any increase thereof.

It is evident from the foregoing experiments that, when the aquatics are goldfishes, (1) death of goldfishes due to the inflow of toxic materials can be judged by measuring the $CO_2$ concentration, and (2) the inflow of toxic materials can be detected from an absolute value or change in rate of the $CO_2$ concentration. In the foregoing experimental results, it is confirmed that the detection of a change in water quality due to the inflow of cyanide is possible at an early stage, and the same things are applicable to other toxic materials and other aquatics. As described above, a change in water quality can be detected at an early stage by measuring a $CO_2$ concentration accompanying the respiratory activity of the aquatics.

The present invention is based on said basic concept, and one embodiment of the present invention will be described below, referring to FIG. 3.

Figure 3:
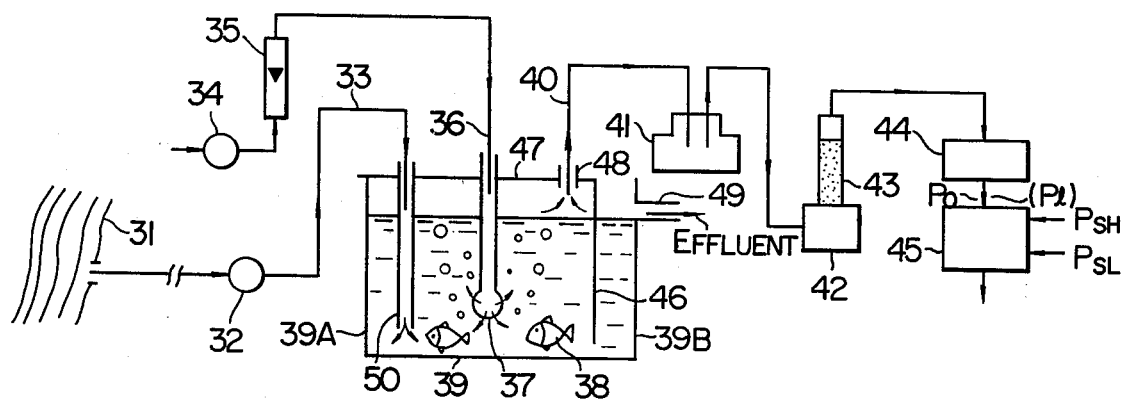
FIGS. 3-5 are schematic flow diagrams showing different embodiments of the present invention.

In FIG. 3, water 33 is introduced from a water source 31 into a water bath 39 by a sampling pump 32. One end of a tube 50 for introducing water is located at the bottom of the water bath 39, and, that is, water is supplied from the bottom of the water bath, and thus the water 33 is sufficiently stirred thereby. Air 36 is introduced into the water bath 39 through a flow rate meter 35 and an air stone 37 by an air blowing means such as an air pump 34.

A partition plate 46 is provided in the water bath 39, and a space between the partition wall 46 and side walls 39A of the water bath 39 is tightly sealed by a cover 47, whereas a space between the partition plate 46 and side walls 39B is open to the atmosphere, and an effluent passage 49 is provided at the side wall 39B. Thus, the water level of the water bath 39 is always constant and equal to the level of the effluent passage 49. A clearance between the lower end of the partition plate 46 and the bottom surface of the water bath 39 is adjusted to such a value as not to allow the goldfishes 38 to enter the chamber open to the atmosphere. Goldfishes are bred in the water bath 39, and $CO_2$ produced by the respiration of goldfishes 38 is dissipated into the gas phase section of the water bath 39 together with the air 36, and led as a sample gas 40 to a $CO_2$ meter 44 from a sample gas outlet 48 through a moisture remover 41 and a silica gel packed column 42 filled with silica gel 43 as a dehumidifier. As the $CO_2$ meter 44, a non-dispersing type infrared spectrometer is used to measure a $CO_2$ content, Pl, of the sample gas 40, that is, $CO_2$ concentration $P_O$, where that of the air 36 is always constant. Numeral 45 is a comparator, which can compare the actually measured value, $P_O$, with set values, $P_{SH}$ and $P_{SL}$, of $CO_2$ concentration, and produce an output when $P_O > P_{SH}$ or $P_O < P_{SL}$.

In such a structure, water 33 is continuously supplied to the water bath 39 from the water source 31 by the sampling pump 32, and introduced from the lower part of the water bath 39 through the tube 50, whereas air 36 is supplied at a constant rate to water to the water bath 39 through the air stone 37 by the air pump 34.

When no toxic materials are contained in the water 33 introduced from the water source 31, the rate of $CO_2$ produced by the respiration of goldfishes 38 is constant, that is, the $CO_2$ production rate by daily activities of the goldfishes 38 does not undergo large change, and is kept almost constant. $CO_2$ thus produced is led to the $CO_2$ meter 44 as a sample gas. The rate of air supplied by the air pump 34 is constant, and air is not soluble in water. Thus, the rate of $CO_2$ produced by the goldfishes, that is, $CO_2$ concentration, can be determined by measuring the $CO_2$ content of the sample gas 40. The actually measured value $P_O$ of the $CO_2$ concentration is compared with set values, $P_{SH}$ and $P_{SL}$, in the comparator 45. The set value $P_{SH}$ is set to a little higher value than the concentration of $CO_2$ produced by the daily activity of goldfishes 38, and the set value $P_{SL}$ to a little lower value than that of $CO_2$ produced by the daily activity of goldfishes. In that case, $P_{SL} < P_O < P_{SH}$, and the comparator 45 does not produce an output.

When the water introduced from the water source 31 contains toxic materials soluble in water, the respiratory activity of goldfishes 38 in the water bath 39 changes, and also the $CO_2$ production rate changes. Thus, the $CO_2$ concentration measured by the $CO_2$ meter 44 changes. When the concentration of toxic materials is so high that the goldfishes 38 die instantaneously, the $CO_2$ production rate is decreased to zero. When the concentration of toxic materials is low, the respiratory activity of goldfishes 38 becomes vigorous, and consequently the $CO_2$ production rate is increased. When the water quality changes due to the inflow of toxic materials, the rate of $CO_2$ produced by the respiratory activity of goldfishes will change in some way.

If the $CO_2$ production rate is increased, the $CO_2$ concentration $P_O$ measured by the $CO_2$ meter 44 will be in a relation of $P_O > P_{SH}$. The comparator 45 thus produces an output, and the change in water quality can be detected.

If the $CO_2$ production rate is decreased to the contrary, a relation of $P_O < P_{SL}$ will be established, and the comparator 45 similarly produces an output. A change in water quality is detected in this manner, and the change in the $CO_2$ production rate due to the change in water quality is larger than that due to the daily biological activities such as eating, sleeping and movement, of goldfishes 38, and can be clearly distinguished.

The moisture remover 41 and the silica gel packed column 42 are to remove moisture from the sample gas 40 and thereby prevent the lowering of exactness in detection of the $CO_2$ meter. Since the infrared absorption zone of $CO_2$ is partly overlapped with that of water, the lowering of exactness in detection due to the partial overlapping must be prevented.

The change in the water quality is detected in said manner only by measuring the $CO_2$ concentration, and thus an on-line measurement is possible. Furthermore, only the gas is collected to measure the $CO_2$ concentration of the gas, and thus the apparatus itself will have a simple structure, resulting in easy maintenance and inspection.

In the foregoing description, water 33 is continuously introduced into the water bath 39 from the water source, but can be intermittently introduced thereto. Furthermore, the gas to be supplied to the water in the water bath 39 may be, of course, a nitrogen gas insoluble in water, but the gas must, of course, give no adverse effect upon the biological activities of the goldfishes 38 and must not undergo chemical reaction with $CO_2$.

Figure 4:
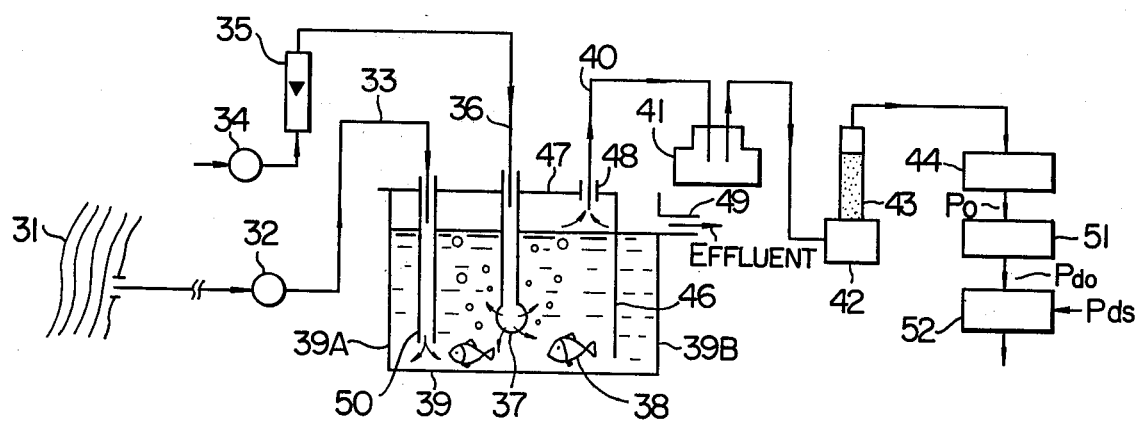

In FIG. 4, another embodiment of the present invention is shown, where a change in water quality is detected from a relation of a rate of change $P_{do}$ in $CO_2$ concentration $P_O$ measured by the $CO_2$ meter 44 to the set value $P_{ds}$.

In detail, the $CO_2$ concentration $P_O$ measured by the $CO_2$ meter 44 is led to a circuit 51 for detecting the rate of change, where the rate of change $P_{do}$ is detected. The detected value $P_{do}$ of the rate of change is compared with the set value $P_{ds}$ in a comparator 52, and a change in water quality is detected, when such a relation as $P_{do} > P_{ds}$ is established.

The $CO_2$ production rate by the daily biological activities of goldfishes 38 is not changed substantially, as shown in FIG. 2, and thus even the rate of change in $CO_2$ concentration can also make a clear distinction and can detect a change in water quality at an earlier stage than the absolute value of the $CO_2$ production rate.

In the embodiments of FIGS. 3 and 4, the $CO_2$ concentration is measured while keeping the rate of air supplied by the air pump 34 constant, and it is presumed that all the amount of the air supplied is contained in the sample gas led to the $CO_2$ meter 44. However, if the air supply rate of the air pump is changed or a gas is soluble in water, there will appear an error in the measured value of $CO_2$ concentration.

Figure 5:
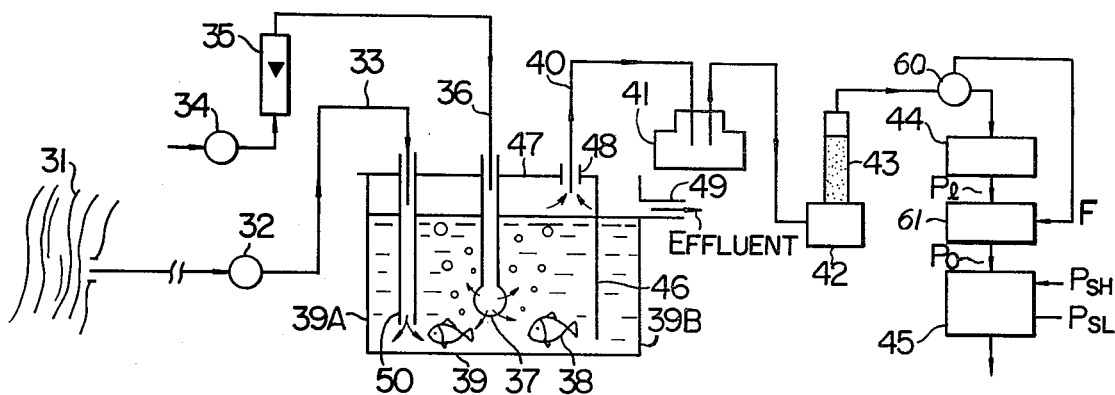

In FIG. 5, further embodiment of the present invention is shown, where such a possible error is eliminated.

Same symbols as in FIG. 3 represent same things also in FIG. 5, except that numeral 60 is a flow rate meter for measuring a flow rate of the sample gas 40, and numeral 61 a multiplier for multiplying the flow rate F of the flow rate meter 60 with the measured value Pl of the $CO_2$ meter 44.

In this embodiment, the flow rate F of the sample gas is measured, and multiplied with the measured value Pl of the $CO_2$ meter 44 in the multiplier 61 to determine $CO_2$ concentration $P_O$. Even if the rate of air supplied by the air pump 34 is changed, or a water-soluble gas other than air is used, the $CO_2$ concentration $P_O$ can be exactly measured. A change in water quality can be detected in the same manner as in the embodiment of FIG. 3 by putting the output from the multiplier 61 to the comparator 45. It is readily comprehensible that a change in water quality can be detected also from a rate of change in the $CO_2$ concentration thus measured.

$CO_2$ can adjust pH and chemical composition of natural water by biochemical exchange between water and biological organisms. Thus, when only the rate of $CO_2$ produced by the respiratory activity of the aquatics is to be determined, it is necessary to take into account the changes in the dissociation state of carbonic acid accompanying changes in pH and composition of water, that is, the decarbonation action.

Figure 6:
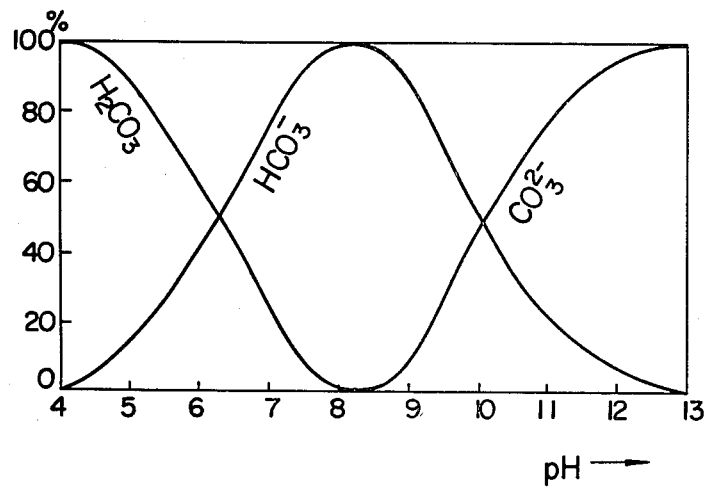
FIG. 6 is a characteristics diagram showing relations between states of dissociation of carbonic acid and pH.

In FIG. 6, well-known relations between the dissociation state of carbonic acid and pH are shown. It is apparent from FIG. 6 that there mainly exist bicarbonate ions $HCO_3^-$ and carbonate ions $CO_3^{2-}$ at pH of 8 or higher, and carbonic acid $H_2CO_3$ ($H_2O + CO_2$) at lower pH. When acidic toxic materials such as $CuSO_4$ happen to be contained in water, pH and alkalinity are lowered and consequently decarbonation action takes place to generate $CO_2$ from water.

Figure 7:
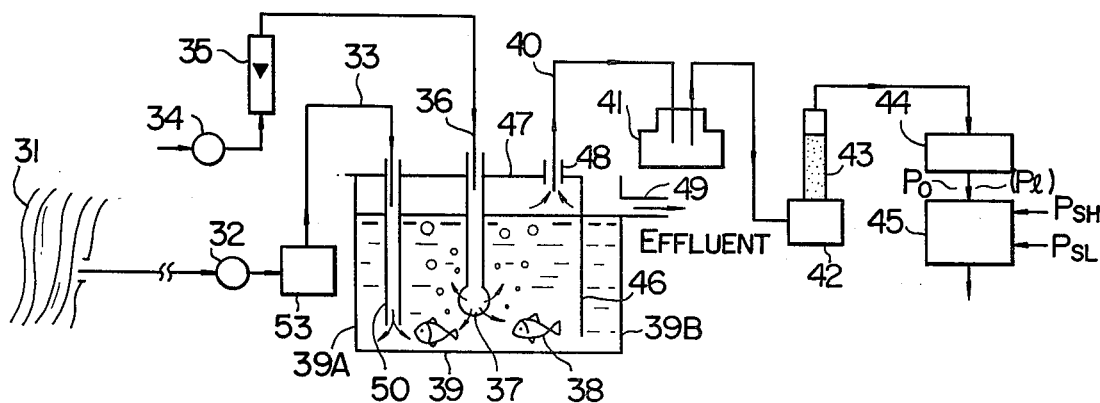
FIG. 7 is a schematic flow diagram showing another embodiment of the present invention.

In FIG. 7, an embodiment of measuring only $CO_2$ production rate by the respiratory action of goldfishes while removing $CO_2$ generated by the decarbonation action is shown, where water to be introduced to the water bath is decarbonated in advance to bring water always in the chemical equilibrium.

Only difference of the embodiment of FIG. 7 from that of FIG. 3 is in introducing water 33 from the water source 31 to the water bath 39 through a decarbonator 53.

Figure 8:
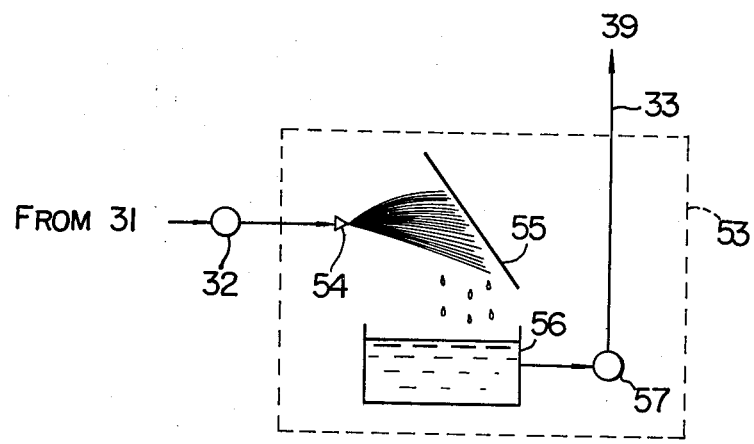
FIG. 8 is a schematic detail of an embodiment of decarbonator in FIG. 7.

In FIG. 8, detail of one embodiment of the decarbonator 53 is shown, where water introduced from the water source 31 by the pump 32 is led to a nozzle 54 and made to vigorously impinge on a baffle board 55 from the nozzle 54. $CO_2$ contained in water is decarbonated to a concentration in equilibrium with the atmosphere. Water decarbonated to the chemical equilibrium is reserved in a tank 56, and then led to the water bath by a pump 57.

The portion of $CO_2$ generated by the inflow of the acidic toxic materials can be removed by decarbonating water in such decarbonator 53 as shown in FIG. 8, and supplying the decarbonated water to the water bath 39. Thus, $CO_2$ contained in the sample gas 40 corresponds to $CO_2$ produced only by the respiratory action of goldfishes 38, and $CO_2$ can be exactly measured. That is, a change in water quality can be more precisely detected thereby.

Figure 9:
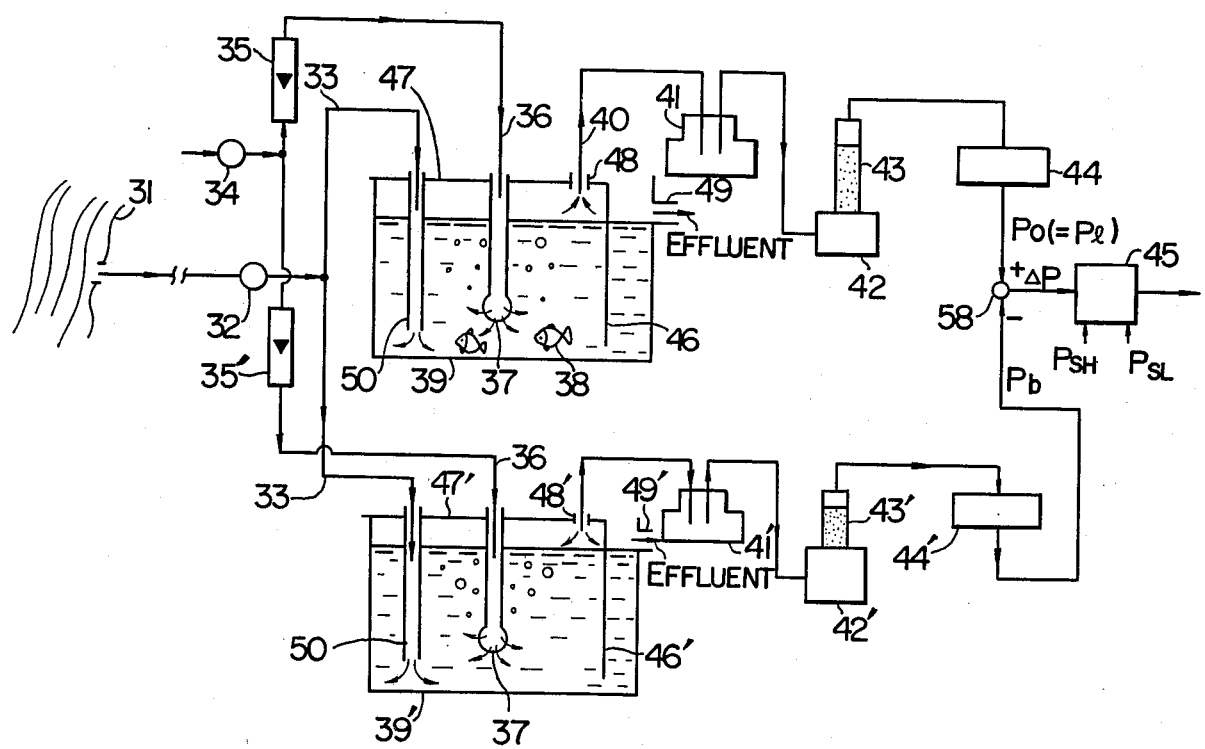
FIG. 9 is a schematic flow diagram showing another embodiment of the present invention.

In FIG. 9, another embodiment of removing the influence of $CO_2$ generated by the decarbonation action is shown, where a water bath without breeding goldfishes is additionally provided to determine a background value of $CO_2$ concentration.

Same symbols as in FIG. 3 show the same things in FIG. 9, but numerals for the devices for determining the background value of $CO_2$ concentrations of water 33 are dashed with a mark (,) on their right upper ends. Water bath 39' is of the same structure and the same capacity as the water bath 39, but no goldfish is bred in the water bath 39'. Numeral 58 is a subtractor for making a subtraction between the measured values $P_O$ and $P_b$ by the $CO_2$ meters 44 and 44', respectively.

In the embodiment of FIG. 9, water is introduced to the water baths 39 and 39' from the water source 31 at an equal flow rate, and the water baths 39 and 39' are of the same specification, and their water levels are identical to each other. Air is supplied to these two water baths at an equal flow rate by the air pump 34.

When no toxic materials are contained in water 33, the value $P_O$ measured by the $CO_2$ meter 44 represents the $CO_2$ production rate by the daily biological activities of goldfishes and is almost constant. On the other hand, the $CO_2$ production rate in the water bath 39' corresponds to $CO_2$ contained in water 33, and the value $P_b$ measured by the $CO_2$ meter 44' depends upon the $CO_2$ content of water 33.

The values $P_O$ and $P_b$ measured by the $CO_2$ meters 44 and 44', respectively, are subjected to subtraction by the subtractor 58 according to the polarity shown in FIG. 9. The subtracted value $\Delta P$ corresponds to the $CO_2$ production rate by the daily biological activities of goldfishes 38, and is almost constant. The subtracted value $\Delta P$ is compared in the comparator 45, and since $P_{SL} < \Delta P < P_{SH}$ in that case, the comparator 45 produces no output.

If water 33 contains toxic materials, the subtracted value $\Delta P$ from the subtractor 58 will be in such a relation as $\Delta P > P_{SH}$ or $\Delta P < P_{SL}$. Thus, the comparator 45 produces an output, and a change in water quality can be detected.

As described above, the $CO_2$ concentration of only the respiratory activity of goldfishes can be obtained by subtracting the background value of the concentration of $CO_2$ contained in the sample water from the $CO_2$ concentration from the water bath breeding the goldfishes. Thus, the $CO_2$ concentration can be exactly measured, and as a result, the exactness in detection of a change in water quality can be improved.

In the embodiments of FIGS. 7 and 9, air is supplied to the water bath at a constant flow rate. However, if the air flow rate of the air pump is changed or a gas is soluble in water, it is, of course, also possible that the sample gas flow rate is measured and multiplied by the value measured by the $CO_2$ meter to measure the $CO_2$ concentration as described in the embodiment of FIG. 5.

In the present invention, a change in water quality can be simply detected on line by measuring the $CO_2$ concentration accompanying the respiratory activity of aquatics, as described above. Furthermore, only the gas is collected to measure the $CO_2$ concentration of the gas, and thus the apparatus itself will have a simple structure, resulting in easy maintenance and inspection.

Since a change in water quality is detected by measuring changes in $CO_2$ concentration due to the respiratory action of aquatics in the present invention, the present invention is applicable not only to such aquatics as fishes, but, of course, also to such aquatics as plankton, microorganisms, etc.

In the foregoing embodiments, an effluent passage is provided at the water bath to make the water level of the water bath constant to obtain an exact $CO_2$ concentration. However, it is apparent to make the water level constant by providing a discharge pump in the water bath without the effluent passage. Furthermore, not only air or nitrogen gas, but also any gas, so long as it has no adverse effect upon the aquatics, can be, of course, used as the gas for stirring the water in the water bath. Practically, air is preferable.

What is claimed is:

1. An apparatus for detecting a change in water quality by using biological activities of fish, which comprises:
   (a) a water bath to which sample water is introduced, said water bath having fish living therein, the water bath comprising a chamber tightly sealed to the atmosphere and a chamber open to the atmosphere, the two chambers being partitioned by partition means having a lower end at a clearance from a bottom surface of the water bath and preventing said fish from entering the chamber open to the atmosphere, and an effluent passage provided at the chamber open to the atmosphere, the fish generating carbon dioxide during their biological activities, whereby the carbon dioxide generated by said fish changes depending on the water quality of the sample water introduced in said water bath,
   (b) a gas-supplying means for supplying a gas having no adverse effect upon the biological activities of the fish to water in said water bath, and for stirring the water,
   (c) a collecting means for collecting the gas supplied by the gas-supplying means to the water in the water bath and carbon dioxide, generated by the biological activities of the fish, dissipated from the water in the water bath as a sample gas,
   (d) a carbon dioxide-measuring means for measuring concentration of carbon dioxide in the sample gas collected by said collecting means, and
   (e) a concentration change-detecting means for detecting a change in the concentration of the carbon dioxide as measured by said carbon dioxide measuring means, whereby a change in water quality can be detected by detecting the change in carbon dioxide concentration in said sample gas.

2. An apparatus according to claim 1, further including a supply of air connected to the gas-supplying means, whereby the gas supplied to the water in the water bath by the gas-supplying means is air.

3. An apparatus according to claim 1, further including a supply of nitrogen connected to the gas supplying means, whereby the gas supplied to the water in the water bath by the gas-supplying means is a nitrogen gas.

4. An apparatus according to claim 1, wherein the gas-supplying means includes means to supply the gas at a constant rate to the water bath.

5. An apparatus according to claim 1, wherein the collecting means includes means to remove moisture from the sample gas.

6. An apparatus according to claim 1, wherein the carbon dioxide-measuring means is a non-dispersing type infrared spectrometer for measuring a carbon dioxide content of the sample gas.

7. An apparatus according to claim 1, wherein the concentration change-detecting means comprises means to detect a change in carbon dioxide concentration by absolute value of carbon dioxide concentration.

8. An apparatus according to claim 1, wherein the concentration change-detecting means comprises means to detect a change in carbon dioxide concentration by rate of change in carbon dioxide concentration.

9. An apparatus according to claim 1, further comprising means for sending the value of the measurement of the concentration of carbon dioxide, as measured by said carbon-dioxide measuring means, to said concentration change-detecting means.

10. An apparatus for detecting a change in water quality by using biological activities of aquatics, which comprises:
   (a) a water bath adapted for the aquatics to live in and to which sample water is introduced,
   (b) a gas-supplying means for supplying a gas having no adverse effect upon the biological activities of the aquatics to water in said water bath, and for stirring the water,
   (c) a collecting means for collecting the gas supplied by the gas-supplying means to the water in the water bath and carbon dioxide, generated by the biological activities of the aquatics, dissipated from the water in the water bath as a sample gas,
   (d) a carbon dioxide-measuring means for measuring concentration of carbon dioxide in the sample gas collected by said collecting means,
   (e) a concentration change-detecting means for detecting a change in measured concentration of the carbon dioxide, whereby a change in water quality can be detected by detecting the change in carbon dioxide concentration in the sample gas, and
   (f) a decarbonator for decarbonating the sample water and supplying the decarbonated water to the water bath.

11. An apparatus for detecting a change in water quality by using biological activities of aquatics, which comprises:
   (a) a water bath adapted for the aquatics to live in and to which sample water is introduced,
   (b) a gas-supplying means for supplying a gas having no adverse effect upon the biological activities of the aquatics to water in said water bath, and for stirring the water,
   (c) a collecting means for collecting the gas supplied by the gas-supplying means to the water in the water bath and carbon dioxide, generated by the biological activities of the aquatics, dissipated from the water in the water bath as a sample gas,
   (d) a carbon dioxide-measuring means for measuring concentration of carbon dioxide in the sample gas collected by said collecting means,
   (e) a gas flow rate meter for measuring a flow rate of the sample gas to the carbon dioxide-measuring means,
   (f) a multiplying means for multiplying value measured by the carbon dioxide-measuring means by measured value of the flow rate of the sample gas, whereby an adjusted concentration of carbon dioxide is obtained, and
   (g) a concentration change-detecting means for detecting a change in the adjusted concentration of carbon dioxide, whereby a change in water quality can be detected by detecting the change in adjusted concentration of carbon dioxide.

* * * * *